US00PP23474P2

(12) United States Plant Patent
Leue

(10) Patent No.: US PP23,474 P2
(45) Date of Patent: Mar. 12, 2013

(54) *HEUCHERA* PLANT NAMED 'MAROON BLUSH'

(50) Latin Name: *Heuchera×hybrida*
Varietal Denomination: Maroon Blush

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 113 days.

(21) Appl. No.: 13/134,014

(22) Filed: May 26, 2011

(51) Int. Cl.
*A01H 5/00* (2006.01)

(52) U.S. Cl. ..... Plt./440

(58) Field of Classification Search ..... Plt./440
See application file for complete search history.

(56) References Cited

PUBLICATIONS

*Heuchera* 2011 Perennial Catalog DarwinPerennials, retrieved on Oct. 23, 2012, retrieved from the Internet at <http://www.who-sells-it.com/cy/ball-horticultural-4605/2011-darwin-perennials-22272/page-1.html>, p. 71.*

* cited by examiner

*Primary Examiner* — June Hwu
(74) *Attorney, Agent, or Firm* — Audrey Charles

(57) ABSTRACT

A new and distinct cultivar of *Heuchera* plant named 'Maroon Blush', characterized by its medium rosy-tan colored mature foliage having prominent brown venation and a silvery appearance, white-pink colored flowers, and moderately vigorous, mounded growth habit, is disclosed.

1 Drawing Sheet

Latin name of genus and species of plant claimed: *Heuchera×hybrida.*

Variety denomination: 'Maroon Blush'.

BACKGROUND OF THE INVENTION

The present invention relates to a new and distinct cultivar of *Heuchera* plant botanically known as *Heuchera×hybrida* and hereinafter referred to by the cultivar name 'Maroon Blush'.

The new cultivar originated in a controlled breeding program in Elbum, Ill. during May 2009. The objective of the breeding program was the development of *Heuchera* cultivars with improved vigor and vivid foliage coloration.

The new *Heuchera* cultivar is the result of open-pollination. The female (seed) parent of the new cultivar is the proprietary *Heuchera×hybrida* breeding selection designated 227m-4, not patented, characterized by its white-colored flowers, light rosy-tan colored foliage, and moderately vigorous, mounded growth habit. The male (pollen) parent of the new cultivar is unknown. The new cultivar was discovered and selected as a single flowering plant within the progeny of the above stated open-pollination during April 2010 in a controlled environment in Elburn, Ill.

Asexual reproduction of the new cultivar by in vitro propagation since April 2010 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Maroon Blush' as a new and distinct cultivar of *Heuchera* plant:

1. Medium rosy-tan colored mature foliage having prominent brown venation and a silvery appearance;
2. White-pink colored flowers; and
3. Moderately vigorous, mounded growth habit.

Plants of the new cultivar differ from plants of the female parent primarily in intensity of foliage color.

Of the many commercially available *Heuchera* cultivars, the most similar in comparison to the new cultivar is the cultivar 'Peach Flambe', U.S. Plant Pat. No. 17,195. However, in side by side comparisons, plants of the new cultivar differ from plants of 'Peach Flambe' in at least the following characteristics:

1. Plants of the new cultivar have darker-colored foliage venation than plants of 'Peach Flambe'; and
2. Plants of the new cultivar have foliage with a silver appearance unlike foliage of plants of 'Peach Flambe'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Maroon Blush'. The plant was grown in a 10 cm pot for approximately 4 months and then finished in a 19 cm container for approximately 2 months in a greenhouse located in Hillegom, The Netherlands.

DETAILED BOTANICAL DESCRIPTION

Figure 1:
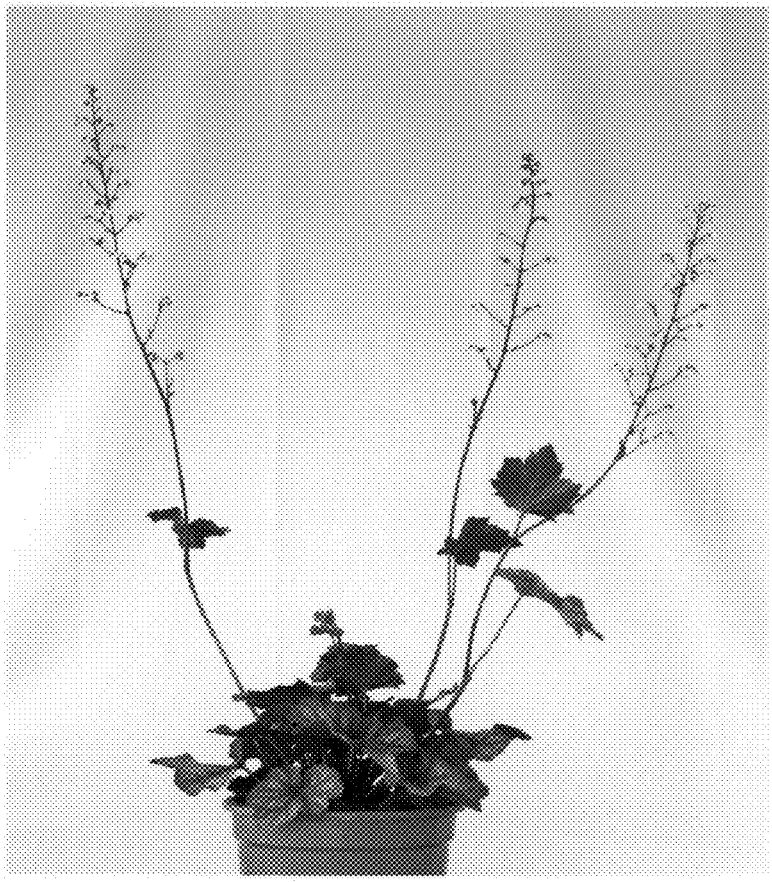
FIG. 1 illustrates a side view of the overall growth and flowering habit of 'Maroon Blush'.
Figure 2:
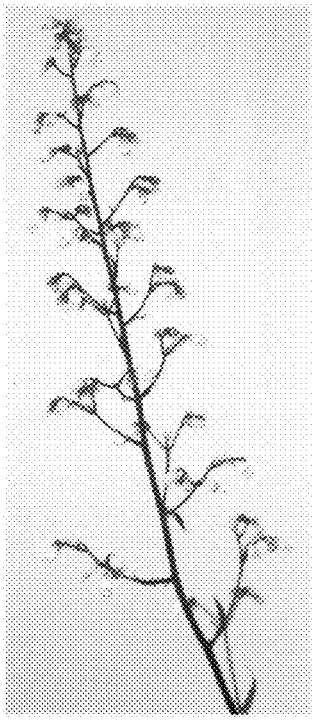
FIG. 2 illustrates a close-up view of an individual inflorescence of 'Maroon Blush'.
Figure 3:
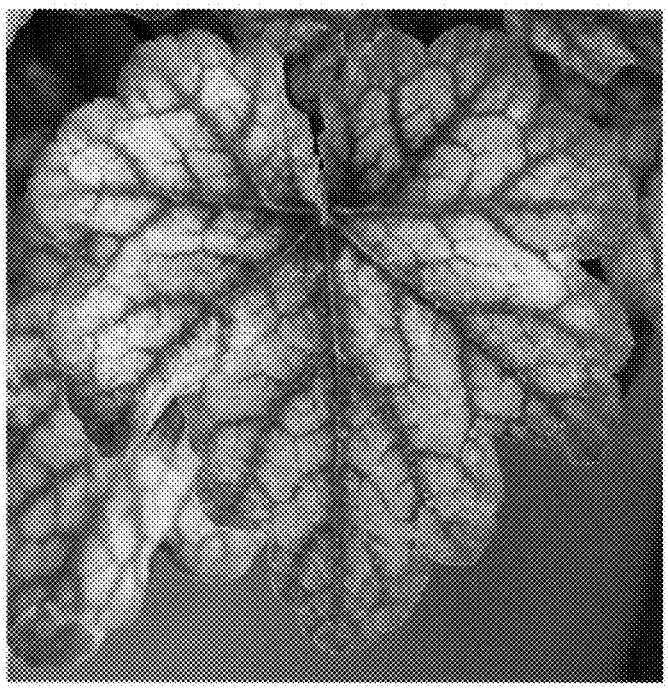
FIG. 3 illustrates a close-up view of the foliage of 'Maroon Blush'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2011 under natural light conditions in Hillegom, The Netherlands.

The following descriptions and measurements describe plants produced from in vitro propagated plants in a 10 cm pot for approximately 4 months and then finished in a 19 cm container for approximately 2 months in a plastic-covered greenhouse located in Hillegom, The Netherlands. The plants were grown under conditions comparable to those used in commercial practice having for the last 2 months average day temperatures of 14° C. to 27° C. and average night temperatures of 6° C. to 18° C.

Botanical classification: *Heuchera×hybrida* cultivar Maroon Blush.

Parentage:

*Female parent*.—227m-4, not patented.

*Male parent*.—Unknown.

Propagation:

*Type*.—In vitro propagation is preferred, divisions are possible.

*Time to initiate roots in vitro*.—Approximately 10 days at 20° C.

*Time to initiate roots in greenhouse*.—Approximately 20 days at 20° C.

*Time to produce a rooted plantlet in summer*.—Approximately 42 days.

*Root description*.—Fine, fibrous; white to ivory in color.

*Rooting habit*.—Freely branching.

Plant description:

*Commercial crop time*.—Approximately 20 weeks from a rooted tissue culture plantlet to finish in a 10 cm container.

*Growth habit and general appearance*.—Clump-forming herbaceous perennial, mounded foliage.

*Growth rate*.—Moderately vigorous, flowering stems grow approximately 20 cm per month in spring.

*Outdoor plant performance*.—Use as bedding plants or in mixed-container plantings; at least tolerant to temperatures up to 35° C. and hardy to USDA zone 3.

*Size*.—Height from soil level to top of plant plane: Approximately 56.5 cm. Height from soil level to top of foliage: Approximately 13.5 cm. Width: Approximately 39.8 cm.

*Branching habit*.—No branching, basal rosette. Number of basal rosettes per plant: Approximately 1.

Foliage description:

*General description*.—Moderately durable to environmental stresses. Quantity of leaves per rosette: Approximately 33. Fragrance: None. Form: Simple. Arrangement: Alternate.

*Leaves*.—Aspect: Blade is nearly perpendicular to petiole. Shape: Orbicular. Margin: Crenate with an average of 9 lobes per leaf. Apex: Broadly acute. Base: Hastate, moderately overlapping. Venation pattern: Laciniate. Length of mature leaf: Approximately 9.6 cm. Width of mature leaf: Approximately 9.3 cm. Texture of upper surface: Dull; slightly rough. Texture of lower surface: Slightly glossy, slightly rough. Color of upper surface of young, early Spring-like foliage: 178B with venation of 178A. Color of lower surface of young, early Spring-like foliage: 185B with venation of 186A. Color of upper surface of mature foliage: 177D with a heavy overlay of 182B to 182C giving a silvery appearance to the upper surface; venation of 152B to 152C with area that surrounds venation of 200B to 200C. Color of lower surface of mature foliage: 187B to 187C with venation of 186B.

*Stipules*.—Two leafy stipules located at the base of each leaf. Apex: Narrow acute. Length: Approximately 6.0 mm. Width: Approximately 3.0 mm. Color: 71A.

*Petiole*.—Length: Approximately 8.0 cm. Diameter: Approximately 3.0 mm. Texture: Glabrous. Color: 178A.

Flowering description:

*Flowering habit*.—'Maroon Blush' flowers once a year during late spring to midsummer under outdoor conditions.

*Lastingness of individual flower on the plant*.—Approximately 7 days.

Inflorescence description:

*General description*.—Type: Compound spike emerging from the base of the rosette with typically one petiolate cauline leaf. Fragrance: None. Length or height excluding the peduncle: Approximately 21.8 cm. Width: Approximately 7.5 cm. Quantity of inflorescences per plant: Approximately 4. Quantity of fully-opened flowers per inflorescence: Approximately 45. Quantity of flower buds per inflorescence: Approximately 155.

*Peduncle*.—Strength: Strong to moderate. Aspect: Approximately 55° angle from base. Length: Approximately 34.4 cm. Diameter at midpoint: Approximately 3.5 mm. Texture: Moderately pubescent with short glandular hairs of approximately 0.5 mm in length, colored 166A with 197D. Color: Base of 166A with 197A to 197B transitioning to 183A nearest the flowers.

Flower description:

*General description*.—Type: Single, self-cleaning. Aspect: Drooping to slightly outward.

*Bud*.—Rate of opening: Generally takes 3 days for bud to progress from first color to fully open flower.

*Bud just before opening*.—Shape: Broadly elliptic. Length: Approximately 5.0 mm. Diameter: Approximately 2.0 mm. Color: N155C with base of 181B and tip of 179B.

*Corolla*.—Shape: Campanulate. Diameter: Approximately 4.0 mm. Depth: Approximately 8.0 mm.

*Petals*.—Quantity: 5. Arrangement: Rotate. Shape: Narrowly elliptic. Appearance: Dull. Margin: Entire. Apex: Narrow acute. Base: Lower 3.0 mm fused into hypanthium. Length: Approximately 6.0 mm. Width: Approximately 2.0 mm. Texture of upper and lower surfaces: Glabrous. Color of upper and lower surface when first open: 155A with base and tip of 173C to 173D. Color of upper and lower surfaces when fully open: 155A with base and tip of 173C to 173D, color fades to 173B with 184C to 184D.

*Calyx*.—Shape: Cup. Length: Approximately 2.5 mm. Diameter: Approximately 2.5 mm.

*Sepals*.—Quantity per flower: 5. Shape: Elliptic. Appearance: Dull. Margin of free portion: Entire. Apex: Broadly acute. Base: Lower half fused into hypanthium. Length: Approximately 2.5 mm. Width at rim of hypanthium: Approximately 0.6 mm. Texture: Moderately pubescent with very short glandular hairs. Length of pubescence: Approximately 0.1 mm. Color of pubescence: Closest to 184C to 184D. Color of upper and lower surfaces of sepals: 184C.

*Pedicel*.—Strength: Moderate. Aspect: The pedicel of the central flower of each spikelet is directly on top of the secondary pedicel, pedicels of secondary and tertiary flowers of each spikelet have an average 60° angle from vertical. Length of primary pedicels: Approximately 2.2 mm. Length of secondary pedicels: Approximately 2.0 mm. Diameter of primary pedicels: Approximately 0.7 mm. Diameter of secondary pedicels: Approximately 0.3 mm. Texture of all pedicels: Glabrous. Color of all pedicels: 183A.

*Reproductive organs*.—Androecium: Quantity: 5 per flower. Anther shape: Ovate. Anther length: Approximately 0.5 mm. Anther color: 172A. Filament length: Approximately 4.0 mm. Filament color: N155B to N155C. Pollen amount: Moderate. Pollen color: 25A to 25B. Gynoecium: Pistil quantity: 2 per flower. Pistil length: Approximately 5.0 mm. Stigma shape: Pointed. Stigma color: N155B to N155C. Style length: Approximately 3.5 mm. Style color: N155B to N155C. Ovary color: 160B.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Maroon Blush', substantially as herein shown and described.

* * * * *